(12) United States Patent
Gonen

(10) Patent No.: US 7,498,049 B1
(45) Date of Patent: Mar. 3, 2009

(54) TOPICAL TREATMENT OF ACNE WITH COMBINED HERBAL EXTRACTS AND MINERALS

(76) Inventor: Shmuel Gonen, 2 Tnuat HaMeri, Kiryal Ono, 55286 (IL)

( * ) Notice: Subject to any disclaimer, the term of this patent is extended or adjusted under 35 U.S.C. 154(b) by 0 days.

(21) Appl. No.: 11/619,471

(22) Filed: Jan. 3, 2007

(51) Int. Cl.
*A01N 65/00* (2006.01)
*A61K 36/48* (2006.01)

(52) U.S. Cl. ................ 424/725; 424/757
(58) Field of Classification Search ........... None
See application file for complete search history.

(56) References Cited

U.S. PATENT DOCUMENTS

| | | | |
|---|---|---|---|
| 5,409,917 A | 4/1995 | Robinson et al. | |
| 6,300,352 B1 * | 10/2001 | Cheshire et al. | 514/357 |
| 6,977,081 B1 * | 12/2005 | Rood | 424/401 |
| 2001/0021397 A1 * | 9/2001 | Mirsky et al. | 424/725 |
| 2005/0191270 A1 * | 9/2005 | Gruening et al. | 424/78.3 |

FOREIGN PATENT DOCUMENTS

| | | | |
|---|---|---|---|
| JP | 2004250445 | * | 9/2004 |
| WO | WO2004/091638 | * | 10/2004 |

* cited by examiner

*Primary Examiner*—Michael V Meller
*Assistant Examiner*—Qiuwen Mi
(74) *Attorney, Agent, or Firm*—Blakely, Sokoloff, Taylor & Zafman LLP

(57) ABSTRACT

Composition for topical treatment of various forms of acne including (a) 20-40% by volume of an extract of a *GLYCYRRHIZA GLABA* plant; (b) 15-30% by volume of an extract of a *FOENICULUM OFFICINALE* plant; (c) 15-45% by volume of a saturated water solution of at least one mineral salt selected from the group of NaCl,r KCl and $MgCl_2$; and (d) 1-3% by volume of an extract of a *ATRIPLEX HALIMUS* plant.

14 Claims, No Drawings

TOPICAL TREATMENT OF ACNE WITH COMBINED HERBAL EXTRACTS AND MINERALS

FIELD OF THE INVENTION

The present invention generally concerns treatment of human skin disorders and more specifically acne vulgaris. Potentially, the invention is also applicable to other, related skin deceases such as seborrhea and scalp psoriasis.

BACKGROUND OF THE INVENTION

Although the precise causes for the development of acne have not been fully resolved, it has been established that a combination of at-least the following three factors is involved:—
(a) Excessive production of sebum;
(b) Blocking of the entrance of the hair follicle canals; and
(c) Inflammatory processes caused by excessive development of bacteria.

One of the causes for excessive sebum production is the increased activity of androgenic hormones, which is typical to teenagers.

The inflammatory response is a reaction to the follicle canal blocking by keratin plugs.

Conventional topical treating methods generally fall into five major categories:
(a) Application of antiseptics preparations such as various types of soaps and the like detergents.
   This method is disagreeable due to sever skin drying.
(b) Chemical antiseptics such as containing sulfur, which again suffers the disadvantage of skin over-drying.
(c) Compositions such as containing salicylic acid. The disadvantage of these methods resides in causing the skin to become light-sensitive.
(d) Use of vitamin A derivatives commercially known as ROACCUTANE™, CURATANE™, ISOTREX™ and others, which contain tretinoin as active agent.
(e) Antibiotics such as Erythromycin or Benzoyl-Peroxide. Drawbacks and limitations known in connection with other antibiotic medications in the long run may arise including immunity of the body against the efficacy of these drugs.

Oral administered medications have also been tested, mainly in effort to cure the inflammatory of the sebum glands. However, there were found ineffective for removing the white and black heads of the acne comedones.

Attempted use of the new age antibiotics Tetracycline (e.g. MINOCIN™) again, are bound to cause the generally undesirable side-effects of antibiotic treatments.

Another example of orally administered preparations are derivatives of vitamin A, such as ROACCUTANE™. Although reported quite effective, side-effects such as temporary hair loss, sensitivity to sun blaze and joint aches have been experienced; moreover, routine examinations of lever functions must be followed.

Yet another treatment, confined to females only, is based on restricting the sensitivity to the masculine hormone Testosterone.

In extreme cases of inflammation, the use of cortisone has been recommended, albeit for a limited period only.

Experiments with vitamin B or minerals have proved partially successful in reducing sebum production.

For external, night-time application, medications such as DALACIN™, which is based on clindamycin as an active ingredient have been proposed.

For a comprehensive analysis of the prior art see, e.g., U.S. Pat. No. 5,409,917 (Robinson et al).

OBJECTS OF THE INVENTION

It is the main object of the present invention to provide a combined composition for treating of various forms of acne based on natural ingredients.

It is a further object of the present invention that the natural ingredients of the composition will act collectively in eliminating the major symptoms of all types of acne.

It is still a further object of the invention that the composition be health-safe and minimize any undesirable side-effects.

It is still a further object of the invention that the composition be based on herbal extracts, minerals and vitamins.

SUMMARY OF THE INVENTION

According to the invention there is provided a composition for topical treatment of various forms of acne comprising, in one embodiment, 20-40% by volume of an extract of *GLYCYRRHIZA GLABA* plant, 15-30% by volume of alcohol an extract of *FOENICULUM OFFICINALE* plant, 15-45% by volume of saturated water solution of mineral salts selected from the group of NaCl and/or KCl and/or $MgCl_2$ and 1-3% by volume of an extract of *ATRIPLEX HALIMUS* plant.

SPECIFIC DESCRIPTION

In one embodiment, the composition of the invention contains as active agents the following:
(a) The plant *GLYCYRRHIZA GLABA*;
(b) The plant *FOENICULUM OFFICINALE*;
(c) Mineral salts preferably selected from the group of NaCl, KCl and $MgCl_2$ (any one or any combination thereof); alternatively, natural derivatives of the Dead Sea water can be used;
(d) The plant *ATRIPLEX HAUMUS*;
(e) Sulfur
(f) Alcohol (e.g., ethanol)

In more detail:

A. The *GLYCYRRHIZA GLABA* is a plant of the PAPILIONACEAE family.

The active ingredients of this plant are *GLYCYRRHIZIN* and *GLYCYRRHIZIN ACID*.

The selection of this plant is based on the recognition that it's chemical structure presents phyto-estrogen activity which considerably reduces the effect of testosterone which, in turn, reduces the production of sebum; however, being phyto-estrogen, it does not provoke any side-effects associated with the corticosteroid estrogen, even among males.

B. The *FOENICULUM OFFICINALE* is a plant of the UMBELLIFERAE family.

The selection of this plant is based on the recognition that its chemical structure presents cortico-steroid-like properties such as anti-inflammatory properties and improvement of the relationship between estrogen and testosterone.

C. The selection of mineral salts such as NaCl, KCl, and/or $MgGl_2$ is based on the recognition that they contribute to the prevention of the development of bacteria by creating higher osmotic pressure gradient between the outside and the inside of the cells and causes drying-out of the affected area and the bacteria.

D. The plant *ATRIPLEX HALIMUS* (found in arid areas) is salt-rich thus also increasing the osmotic pressure of cells.

E. Sulfur (e.g., elemental sulftur) and alcohol are known for their anti-septic activity.

In one embodiment, extracts of the *GLYCYRRHIZA GLABA* plant, the *FOENICULUM OFFICINALE* plant, and the *ATRIPLEX HALIMUS* plants are prepared by admixing components of the individual plants with elemental sulfur and a solvent such as 95% ethyl alcohol. Dry, shredded roots of the *GLYCYRRHIZA GLASA* plant, for example, are mixed with an amount of elemental sulfur ranging from 2% to 45% by volume sulfur, in one embodiment from 2% to 8% by volume, in another embodiment 35% to 45% by volume. Dry, shredded plant grains of the *FOENICULUM OFFICINALE* plant, for example, are admixed with an amount of elemental sulfur ranging from 2% to 35% by volume sulfur, in one embodiment, from 2% to 8% by volume, in another embodiment, from 25% to 35%. The ground *ATRIPLEX HALIMUS* plant, for example, is admixed with an amount of elemental sulfur ranging from 1% to 250% by volume sulfur, in one embodiment, 1% to 3% by volume, and in another embodiment, 250% by volume sulfur, in one embodiment, 1% to 3% by volume, and in another embodiment, 250% by volume. The admixed extracts are then combined with mineral salts in a final composition. In one embodiment, the overall mineral salts is between 1-15% of the composition; the overall volume of alcohol is between 5-60%; and the overall volume of sulfur is between 1-15%.

PREPARATION EXAMPLES

I—A Quantity of 5 lit. of *Glycyrrhiza Glaba* Extract is Prepared as Follows (1) dry-shredding of the plant roots;
(2) Mixing 600 gr. of the *GLYCYRRHIZA GLABA* shred with 250 gr. of sulfur powder (elemental sulfur) in a 5 lit. container.
(3) Topping the container with ethyl alcohol 95% solvent; and
(4) Stirring the mixture for 15 days.

II—A Quantity of 5 lit. of *Foeniculum Officinale* Extract is Prepared as Follows (1) dry-shredding of the plant grains;
(2) Grinding the plant grains shred to flour-like powder;
(3) Mixing 800 gr. of the plant powder with 250 gr. of sulfur powder in a 5 lit. container;
(4) Topping the container with ethyl alcohol 950% solvent; and
(5) Stirring the mixture for 15 days.

III—A Quantity of 5 lit. of *Atriplex Halimus* Extract is Prepared as Follows (1) Drying the plant to a grindable stage;
(2) Grinding into fine flour-like powder;
(3) Mixing 50 gr. of the plant powder with 100 gr. of sulfur powder in a 5 lit. container;
(4) Adding 2 lit. of water;
(5) Adding 2.5 lit. of ethyl alcohol 95% solvent; and
(6) Stirring the mixture for 15 days.

IV—A Quantity of 5 lit. of Mineral(s) Solution is Prepared as Follows (1) 2.0 Kg. of the minerals NaCl, KCl and $MgCl_2$ (or any one or any combination thereof) in a 5 lit. container;
(2) Adding 1.5 lit. of water;
(3) Placing for 5 days for initial dissolution;
(4) Adding 100 gr. of sulfur powder under continuous stirring;
(5) Topping the container with ethyl alcohol 95% solvent; and
(6) Stirring the mixture for 10 days.

V—5 lit. of the Final Product are Prepared as Follows (1) Pouring 1,500 cc of the *GLYCYRRHIZA GLABA* extract into a 5 lit. container;
(2) Adding 990 cc of the *FOENICULUM OFFICINALE* extract;
(3) Adding 100 cc of the *ATRIPLEX HALIMUS* extract;
(4) Adding 2,000 cc of the mineral(s) solution;
(5) Adding 400 cc of ethyl alcohol 95% solvent;
(6) Stirring for 20 min.
(7) Straining the mixture for removing remaining plants residue or other sediments; and, optionally,
(8) Adding about 10 cc of vitamin E and/or yeast.

Results of Treatment

The results of tests listed below were conducts at the INSTITUTE FOR SKIN RESEARCH in Tel Aviv, Israel, under the terms of the ETHICA COMMITTEE (Helsinki Committee), supervised by Professor (Dermatology) Sarah Brenner.

Tested were conducted on a population of 30 volunteers, ranging from 14 to 42 years old, of which 9 males and 21 females.

The composition of this invention was applied to the face twice a day (morning and evening) for 4 weeks.

The results are given in Appendix A hereto.

The reported summary of the research reads as follows:

"At the end of the 4 week period of treatment there was a significant decrease in all the examined parameter's values, which imply a significant improvement.

Treatment of the tested product significantly decreased the number of comedones after two weeks, this decrease continued also after 4 weeks.

Treatment of the tested product significantly decreased the number of papules after two weeks, this decrease continued also after 4 weeks.

There wasn't a significant change in the number of pustules after 2 weeks of treatment, but a significant decrease in the number of pustules was found after 4 weeks of treatment with the tested product."

It is believed that the excellent yielded results are due to the unique combination of elements as above described, wherein the effect of each element is directed to a different angle of attacking the basic causes of acne.

It will be appreciated by those skilled in the art, that the invention has been described hereinabove with reference to certain examples and specific embodiments. However, these are not the only examples and embodiments in which the invention may be practiced. Indeed, various modifications may be made to the above-described examples and embodiments without departing from the intended spirit and scope of the present invention, and it is intended that all such modifications be included within the scope of the following claims.

APPENDIX A

| Vol. Number | Initials | Age | First visit The beginning of the experiment | | | | Second visit After 14 days of treatment | | | | Third visit After 28 days of treatment | | | |
|---|---|---|---|---|---|---|---|---|---|---|---|---|---|---|
| | | | Comedones | Papules | Pustules | Acne severity grading | Comedones | Papules | Pustules | Acne severity grading | Comedones | Papules | Pustules | Acne severity grading |
| 1 | R. R | 31 | 68 | 33 | 0 | 1 | 60 | 8 | 2 | 0 | 40 | 3 | 0 | 0 |
| 2 | P. K. | 35 | 50 | 14 | 3 | 2 | 30 | 5 | 0 | 0 | 10 | 4 | 0 | 0 |
| 3 | L. S. | 26 | 80 | 15 | 1 | 2 | 70 | 9 | 1 | 1 | 60 | 8 | 1 | 1 |
| 4 | G. G. | 17 | 40 | 16 | 3 | 2 | 30 | 7 | 2 | 1 | 15 | 2 | 1 | 0 |
| 5 | B. V. | 29 | 33 | 11 | 1 | 3 | 14 | 3 | 0 | 1 | 14 | 1 | 0 | 0 |
| 6 | M. S. | 25 | 40 | 12 | 3 | 4 | 30 | 10 | 0 | 2 | 13 | 4 | 0 | 1 |
| 7 | Y. B. | 28 | 22 | 7 | 2 | 2 | 20 | 6 | 1 | 1 | 12 | 9 | 1 | 1 |
| 8 | A. Y | 17 | 50 | 32 | 0 | 5 | 50 | 23 | 0 | 3 | 50 | 24 | 0 | 3 |
| 9 | M. R. | 26 | 30 | 9 | 0 | 1 | 25 | 3 | 0 | 0 | 21 | 2 | 0 | 0 |
| 10 | S. B. | 22 | 50 | 34 | 1 | 5 | 43 | 22 | 3 | 4 | 36 | 9 | 0 | 2 |
| 11 | S. M. | 15 | 40 | 25 | 7 | 5 | 35 | 20 | 2 | 4 | 29 | 13 | 1 | 3 |
| 12 | S. J. | 32 | 11 | 15 | 2 | 4 | 10 | 9 | 1 | 3 | 15 | 8 | 1 | 3 |
| 13 | R. M. | 15 | 21 | 40 | 4 | 4 | 20 | 40 | 3 | 3 | 24 | 32 | 3 | 3 |
| 14 | R. L. | 32 | 7 | 17 | 0 | 2 | 8 | 5 | 0 | 1 | 3 | 3 | 1 | 1 |
| 15 | M. B. | 15 | 40 | 40 | 6 | 4 | 44 | 14 | 1 | 2 | 20 | 6 | 1 | 1 |
| 16 | O. S. | 14 | 50 | 42 | 0 | 4 | 36 | 23 | 0 | 3 | 31 | 10 | 0 | 1 |
| 17 | D. D. | 16 | 15 | 4 | 1 | 1 | 17 | 5 | 2 | 1 | 6 | 15 | 0 | 1 |
| 18 | A. V. | 34 | 8 | 10 | 0 | 1 | 9 | 7 | 0 | 1 | Missing value | 2 | 0 | 0 |
| 19 | S. E. | 15 | 40 | 20 | 1 | 4 | 38 | 9 | 1 | 3 | 7 | 8 | 1 | 2 |
| 20 | M. E. | 18 | 14 | 30 | 2 | 2 | 14 | 9 | 0 | 1 | 3 | 6 | 0 | 1 |
| 21 | A. D. | 14 | 9 | 22 | 1 | 2 | 7 | 13 | 0 | 1 | 5 | 7 | 0 | 0 |
| 22 | H. K. | 17 | 7 | 10 | 0 | 1 | 8 | 2 | 1 | 0 | 3 | 3 | 0 | 0 |
| 23 | M. D. | 17 | 10 | 45 | 0 | 4 | 7 | 30 | 0 | 3 | 6 | 15 | 0 | 2 |
| 24 | E. E. | 44 | 10 | 8 | 0 | 1 | 10 | 5 | 0 | 1 | 4 | 4 | 0 | 0 |
| 25 | A. K. | 35 | 34 | 13 | 1 | 2 | 11 | 6 | 0 | 2 | 2 | 2 | 0 | 0 |
| 26 | L. A. | 17 | 7 | 12 | 4 | 3 | 6 | 8 | 0 | 2 | 8 | 10 | 1 | 2 |
| 27 | G. H. | 17 | 14 | 18 | 1 | 4 | 17 | 30 | 4 | 4 | 7 | 22 | 2 | 4 |
| 28 | E. S. | 16 | 16 | 38 | 0 | 3 | 6 | 14 | 0 | 2 | 7 | 8 | 0 | 1 |
| 29 | L. E. | 42 | 50 | 8 | 0 | 1 | 4 | 4 | 0 | 1 | 2 | 2 | 0 | 0 |
| 30 | G. N. | 27 | 20 | 14 | 0 | 2 | 14 | 12 | 0 | 2 | Missing values | | | |
| 31 | B. S. | 14 | 50 | 42 | 7 | 5 | 35 | 21 | 7 | 4 | 20 | 25 | 2 | 4 |
| Average | | | 30.19 | 21.16 | 1.65 | 2.77 | 23.48 | 12.32 | 1.00 | 1.84 | 16.31 | 8.90 | 0.53 | 1.23 |

What is claimed is:

1. A composition for topical treatment of various forms of acne comprising an effective amount of an ethanol extract of *Glycyrrhiza glabra* plant, an ethanol extract of a *Foeniculum officinale* plant, a mineral salt and an ethanol extract of an *Atriplex halimus* plant for the topical treatment of various forms of acne, the effective amount comprising:

(a) 20-40% by volume of an ethanol extract of *Glycyrrhiza glabra* plant;
    (b) 15-30% by volume of an ethanol extract of a *Foeniculum officinale* plant;
    (c) 15-45% by volume of a saturated water solution of at least one mineral salt selected from at least one of the group consisting of NaCl, KCl and $MgCl_2$; and
    (d) 1-3% by volume of an ethanol extract of an *Atriplex halimus* plant.

2. The composition of claim 1 further comprising 6-10% by volume of a solvent.

3. The composition of claim 2, wherein the solvent is alcohol.

4. The composition of claim 2 further comprising 8-12% by volume of water.

5. The composition of claim 1, wherein the extract of the *Glycyrrhiza glabra* plant is admixed with 2-8% by volume of sulfur.

6. The composition of claim 1, wherein the extract of the *Foeniculum officinale* plant is admixed with 2-8% by volume of sulfur.

7. The composition of claim 1, wherein the extract of the *Atriplex halimus* plant is admixed with 1-3% by volume of sulfur.

8. The composition of claim 1, wherein the extract of the *Glycyrrhiza glabra* plant is admixed with 35-45% by volume of sulfur.

9. The composition of claim 1, wherein the extract of the *Foeniculum officinale* plant is admixed with 25-35% by volume of sulfur.

10. The composition of claim 1, wherein the extract of the *Atriplex halimus* plant is admixed in 25% by volume of sulfur, and a mixture of about 40% water and 60% by volume of an alcohol.

11. The composition of claim 1, wherein the overall volume of mineral salts is between 5-50%.

12. The composition of claim 1, wherein the overall volume of alcohol is between 5-60%.

13. The composition of claim 1, wherein the overall volume of sulfur is between 1-15%.

14. The composition of claim 1, wherein the extract of the *Glycyrrhiza glabra* plant in the composition consists of an ethanol extract of the root of the *Glycyrrhiza glabra* plant.

* * * * *